(12) United States Patent
Nishio et al.

(10) Patent No.: US 12,376,878 B2
(45) Date of Patent: Aug. 5, 2025

(54) MEDICAL DEVICE

(71) Applicant: TERUMO KABUSHIKI KAISHA, Tokyo (JP)

(72) Inventors: Kosuke Nishio, Irvine, CA (US); Tomonori Hatta, San Jose, CA (US); Taiga Nakano, Irvine, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 979 days.

(21) Appl. No.: 17/326,636

(22) Filed: May 21, 2021

(65) Prior Publication Data

US 2021/0275210 A1 Sep. 9, 2021

Related U.S. Application Data

(63) Continuation of application No. PCT/JP2019/025209, filed on Jun. 25, 2019.

(30) Foreign Application Priority Data

Nov. 21, 2018 (JP) ................................ 2018-218578

(51) Int. Cl.
*A61B 17/3207* (2006.01)
*A61B 17/00* (2006.01)
(Continued)

(52) U.S. Cl.
CPC ...... *A61B 17/320758* (2013.01); *A61B 90/03* (2016.02); *A61B 2017/0042* (2013.01);
(Continued)

(58) Field of Classification Search
CPC .......... A61B 2017/320775; A61B 17/320758; A61B 90/03; A61B 2017/22038;
(Continued)

(56) References Cited

U.S. PATENT DOCUMENTS 5,314,438 A 5/1994 Shturman
6,156,046 A 12/2000 Passafaro et al.
(Continued)

FOREIGN PATENT DOCUMENTS

JP H08509390 A 10/1996
JP 2001522631 A 11/2001
(Continued)

OTHER PUBLICATIONS

International Search Report (PCT/ISA/210) with translation and Written Opinion (PCT/ISA/237) mailed on Aug. 20, 2019, by the Japanese Patent Office as the International Searching Authority for International Application No. PCT/JP2019/025209.

*Primary Examiner* — Ashley L Fishback
(74) *Attorney, Agent, or Firm* — Buchanan Ingersoll & Rooney PC (57) ABSTRACT

A medical device for cutting an object in a body lumen includes: a tubular drive shaft; a cutting unit fixed to a distal portion of the drive shaft; a protective tubular main body accommodated in the drive shaft and the cutting unit and rotatable relative to the drive shaft; and a protective-side stopper disposed on an outer peripheral surface of a distal portion of the protective tubular main body. The distal portion of the drive shaft or the cutting unit has a drive-side stopper contactable with the protective-side stopper. By the protective-side stopper coming into contact with the drive-side stopper, the protective tubular main body is restrained from moving axially with respect to the drive shaft without being restrained from rotating relative to the drive shaft.

20 Claims, 6 Drawing Sheets

(51) Int. Cl.
    *A61B 17/22*     (2006.01)
    *A61B 17/32*     (2006.01)
    *A61B 90/00*     (2016.01)

(52) U.S. Cl.
    CPC ............... *A61B 2017/22038* (2013.01); *A61B 2017/320032* (2013.01); *A61B 2090/036* (2016.02); *A61B 2090/08021* (2016.02); *A61B 2217/005* (2013.01); *A61B 2217/007* (2013.01)

(58) Field of Classification Search
    CPC ......... A61B 2017/320032; A61B 2090/08021; A61B 2217/005; A61B 2217/007
    See application file for complete search history.

(56) References Cited

U.S. PATENT DOCUMENTS

| | | |
|---|---|---|
| 8,394,078 B2 | 3/2013 | Torrance et al. |
| 2016/0354108 A1 | 12/2016 | Nakano et al. |
| 2018/0317952 A1 | 11/2018 | Jamous et al. |

FOREIGN PATENT DOCUMENTS

| | | | |
|---|---|---|---|
| JP | 2002538876 | A | 11/2002 |
| JP | 2016221081 | A | 12/2016 |
| WO | 0054659 | A1 | 9/2000 |

MEDICAL DEVICE

CROSS-REFERENCES TO RELATED APPLICATIONS

This application is a continuation of International Application No. PCT/JP2019/025209 filed on Jun. 25, 2019, which claims priority to Japanese Patent Application No. 2018-218578 filed on Nov. 21, 2018, the entire content of both of which is incorporated herein by reference.

FIELD OF THE DISCLOSURE

The present disclosure relates to a medical device for cutting an object in a body lumen.

BACKGROUND DISCUSSION

A stenosed site attributable to a thrombus, plaque, or a calcified lesion in a blood vessel is treated by, for example, vasodilatation being performed using a balloon or a reticulated or coil-shaped stent being placed in the blood vessel as a blood vessel support. However, it is difficult to treat a stenosed site hardened as a result of calcification and a stenosed site in a bifurcated blood vessel portion by the methods. It is possible to provide treatment even in such a case by, for example, cutting and removing what causes stenosis such as a thrombus, plaque, and a calcified lesion.

U.S. Pat. No. 8,394,078, for example, describes a device in which a cutting unit is disposed at the distal end of a drive shaft to cut what causes stenosis in a blood vessel. A tube that comes into contact with a guide wire is disposed in the cutting unit.

The tube is fixed to the cutting unit in the device described in U.S. Pat. No. 8,394,078. Thus, the tube in the cutting unit rotates together with the cutting unit, and thus a frictional force is generated on the guide wire that comes into contact with the tube. Accordingly, the guide wire may undergo breakage, coating peeling, and so on.

SUMMARY

A medical device is disclosed capable of appropriately protecting a guide wire to be inserted.

In accordance with an aspect, a medical device is disclosed configured to cut an object in a body lumen, the medical device includes: a rotatable and tubular drive shaft; a cutting unit fixed to a distal portion of the drive shaft and having a through-hole communicating with a lumen of the drive shaft; a protective tubular main body accommodated in the drive shaft and the cutting unit and rotatable relative to the drive shaft; a handle rotatably holding a proximal portion of the drive shaft; and a protective-side stopper as a projection on an outer peripheral surface of a distal portion of the protective tubular main body, or a recess in the outer peripheral surface of the distal portion of the protective tubular main body; the distal portion of the drive shaft or the cutting unit includes a drive-side stopper contactable with the protective-side stopper, and the protective tubular main body is restrained from moving in an axial direction with respect to the drive shaft without being restrained from rotating relative to the drive shaft by the protective-side stopper coming into contact with the drive-side stopper.

In accordance with another aspect, a medical device is disclosed for cutting an object in a body lumen, the medical device comprising: a rotatable and tubular drive shaft; a cutting unit fixed to a distal portion of the drive shaft and having a through-hole communicating with a lumen of the drive shaft; a protective tubular main body accommodated in the drive shaft and the cutting unit, the protective tubular main body configured to be rotatable relative to the drive shaft; a protective-side stopper, the protective-side stopper being a projection on outer peripheral surface of a distal portion of the protective tubular main body; the distal portion of the drive shaft or the cutting unit includes a drive-side stopper contactable with the protective-side stopper; and wherein the protective tubular main body is prevented from moving in an axial direction with respect to the drive shaft without being prevented from rotating relative to the drive shaft by the protective-side stopper coming into contact with the drive-side stopper.

In accordance with a further aspect, a medical device is disclosed for cutting an object in a body lumen, the medical device comprising: a rotatable and tubular drive shaft; a cutting unit fixed to a distal portion of the drive shaft and having a through-hole communicating with a lumen of the drive shaft; a protective tubular main body accommodated in the drive shaft and the cutting unit, the protective tubular main body configured to be rotatable relative to the drive shaft; a protective-side stopper, the protective-side stopper being a recess in outer peripheral surface of a distal portion of the protective tubular main body; the distal portion of the drive shaft or the cutting unit includes a drive-side stopper contactable with the protective-side stopper; and wherein the protective tubular main body is prevented from moving in an axial direction with respect to the drive shaft without being prevented from rotating relative to the drive shaft by the protective-side stopper coming into contact with the drive-side stopper.

In accordance with another aspect, a method is disclosed for cutting an object in a body lumen, the method comprising: inserting a guide wire into the body lumen and reaching a vicinity of the object in the body lumen; inserting a proximal end of the guide wire into a guide wire lumen of a medical device; moving the cutting unit to the vicinity of the objection in the body lumen using the guide wire; and rotating the drive shaft and cutting the object with the cutting unit.

The medical device configured as described above is capable of suppressing an excessive distal and/or proximal movement of the protective tubular main body with respect to the cutting unit. Accordingly, the protective tubular main body is capable of appropriately protecting a guide wire inserted into the drive shaft and the cutting unit.

BRIEF DESCRIPTION OF THE DRAWINGS

FIGS. 7A and 7B are cross-sectional views illustrating the distal portion of the medical device, in which FIG. 7A illustrates a first modification example and FIG. 7B illustrates a second modification example.

FIGS. 9A and 9B are plan views illustrating a drive shaft of the medical device, in which FIG. 9A illustrates a fourth modification example and FIG. 9B illustrates a fifth modification example.

DETAILED DESCRIPTION

Set forth below with reference to the accompanying drawings is a detailed description of embodiments of a medical device for cutting an object in a body lumen. Note that since embodiments described below are preferred specific examples of the present disclosure, although various technically preferable limitations are given, the scope of the present disclosure is not limited to the embodiments unless otherwise specified in the following descriptions. It should be noted that dimensions in the drawings may be exaggerated and differ from actual dimensions for convenience of description. In addition, in the present specification and the drawings, components having substantially the same functions are denoted by the same reference numerals for redundant description to be omitted. In the present specification, the side of insertion into the lumen is referred to as "distal side" and the hand side of operation is referred to as "proximal side".

A medical device 10 according to the embodiment can be used for acute lower limb ischemia or deep vein thrombosis treatment by being inserted into a blood vessel and cutting and removing plaque, a calcified lesion, or the like. It should be noted that the object that is cut is not particularly limited and may be, for example, an atheroma, a thrombus, and so on. Further, any object that is capable of existing in a body lumen is capable of corresponding to the object that is cut by the medical device 10.

Figure 1:
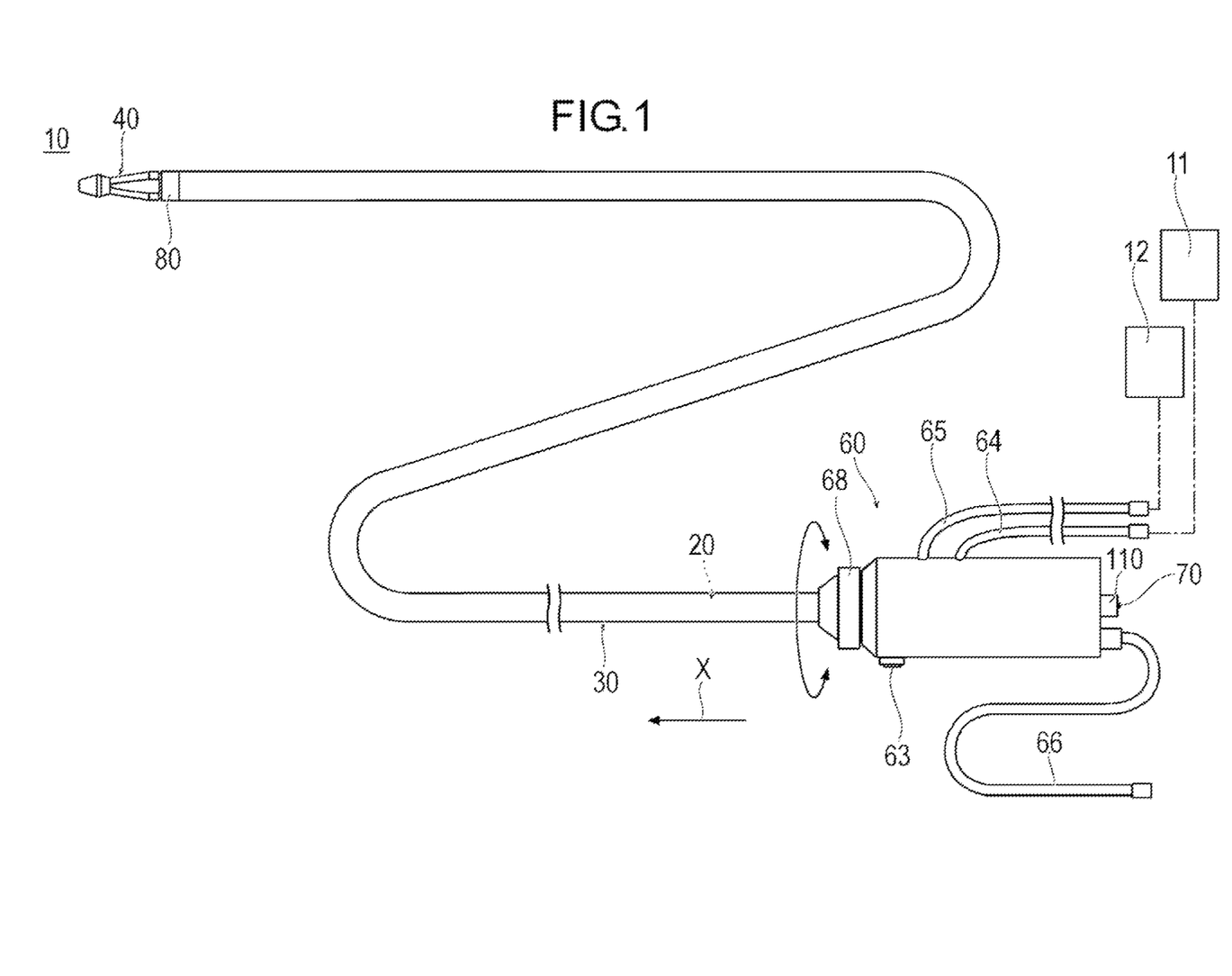
FIG. 1 is a plan view illustrating a medical device according to an embodiment.
Figure 2:
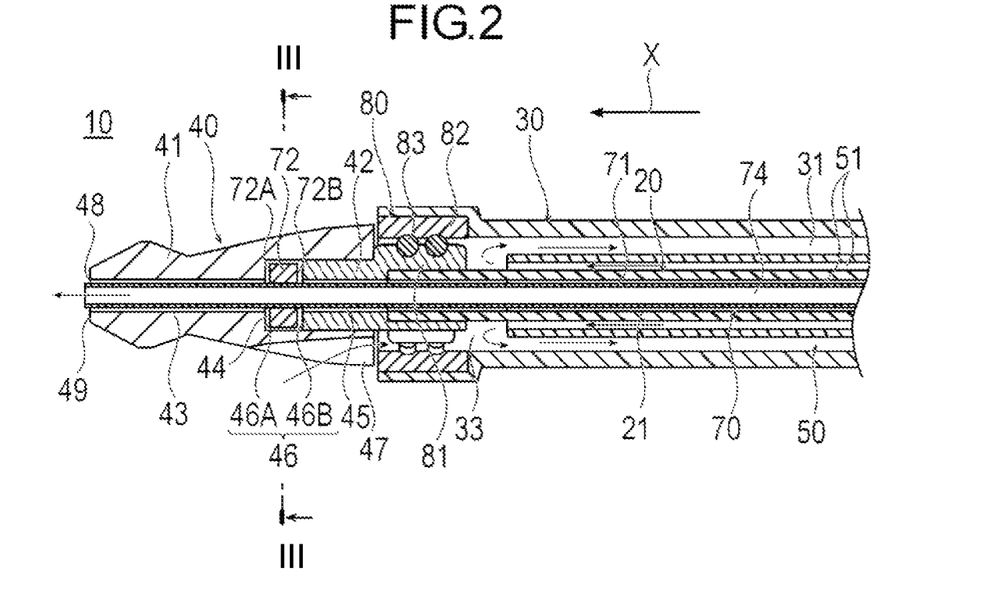
FIG. 2 is a cross-sectional view illustrating a distal portion of the medical device.
Figure 4:
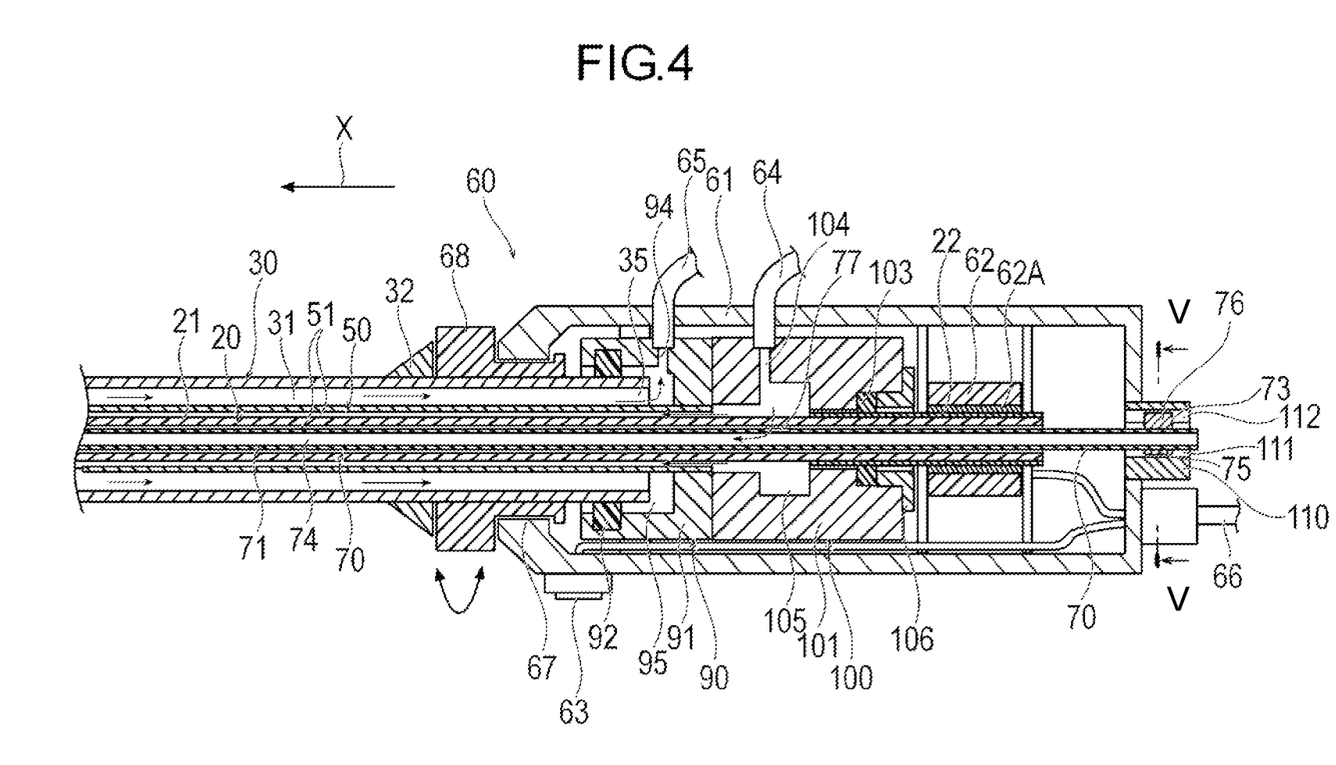
FIG. 4 is a cross-sectional view illustrating a proximal portion of the medical device.

As illustrated in FIGS. 1, 2, and 4, the medical device 10 includes a drive shaft 20 transmitting a rotational force, a protective tube 70 accommodated in the drive shaft 20, an inner tube 50 accommodating the drive shaft 20, and an outer tube 30 accommodating the drive shaft 20 and the inner tube 50. The medical device 10 further includes a cutting unit 40 for cutting plaque or a calcified lesion, and a handle 60.

The drive shaft 20 can be an elongated tubular body and is configured to transmit the rotational force to the cutting unit 40. The drive shaft 20 includes a tubular main shaft 21 and a drive tube 22 fixed to the proximal portion of the main shaft 21.

The main shaft 21 is flexible and capable of transmitting the power of rotation that acts from the proximal side to the distal side. The cutting unit 40 is fixed to the distal portion of the main shaft 21. The main shaft 21 is a tubular body in which a plurality of wire rods are arranged and spirally connected about the shaft center of the drive shaft 20. Accordingly, the main shaft 21 is capable of liquid passage from the gap between the wire rods. The proximal portion of the main shaft 21 is positioned in the handle 60. It should be noted that the main shaft 21 may be configured without a wire rod.

The drive tube 22 is fixed to the proximal portion of the main shaft 21. The drive tube 22 is a rigid tubular body receiving a rotational torque from a drive unit 62 to be described later. In accordance with an exemplary embodiment, the drive tube 22 is configured to transmit the rotational torque received from the drive unit 62 to the flexible drive shaft 20. The drive tube 22 penetrates the drive unit 62 and rotates in the drive unit 62 via a rotating drive rotor 62A of the drive unit 62.

Although the constituent material of the main shaft 21 is not particularly limited, and preferably examples of the material of the main shaft 21 can include stainless steel, nitinol, a fluorine-based polymer such as polytetrafluoroethylene (PTFE) and a tetrafluoroethylene-ethylene copolymer (ETFE), polyetheretherketone (PEEK), polyimide, a polyolefin such as polyethylene and polypropylene, polyamide, and polyester such as polyethylene terephthalate.

The protective tube 70 is disposed in the drive shaft 20 and the cutting unit 40 and is rotatable relative to the drive shaft 20 and the cutting unit 40. As illustrated in FIGS. 2 to 5, the protective tube 70 includes a protective tubular main body 71, a protective-side first stopper 72 as a projecting portion (or projection) disposed in the distal portion of the protective tubular main body 71, and a protective-side second stopper 73 disposed in the proximal portion of the protective tubular main body 71. The protective tubular main body 71 is a flexible tubular body that covers the inner peripheral surface side of the drive shaft 20. The protective tubular main body 71 penetrates the drive shaft 20. The protective-side first stopper 72 is positioned closer to the distal side than the drive unit 62. The protective tubular main body 71 includes a guide wire lumen 74 through which a guide wire may be passed. The guide wire lumen 74 is also a lumen for delivering a liquid such as a saline solution to the distal side. The protective tubular main body 71 helps prevent the guide wire passing through the drive shaft 20 from coming into direct contact with the drive shaft 20 and rubbing. The protective tubular main body 71 may have a side hole 77 penetrating the protective tubular main body 71 between an inner peripheral surface and an outer peripheral surface of the protective tubular main body 71 for liquid passage through the handle 60. The protective tubular main body 71 may have an increased wall thickness in the proximal portion.

Figure 3:
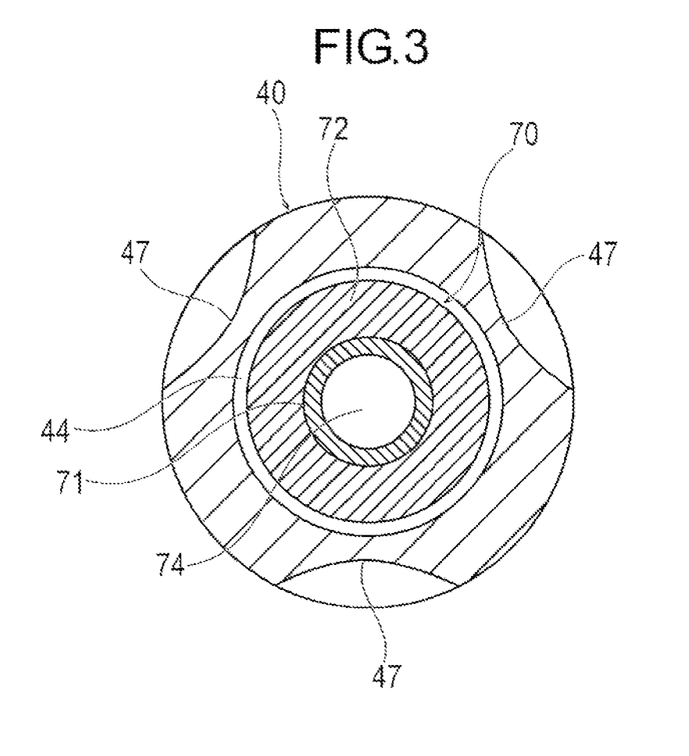
FIG. 3 is a cross-sectional view taken along line III-III of FIG. 2.

As illustrated in FIGS. 2 and 3, the protective-side first stopper 72 is fixed to the outer peripheral surface of the distal portion of the protective tubular main body 71. Accordingly, the protective-side first stopper 72 rotates together with the protective tubular main body 71. The protective-side first stopper 72 helps restrain the protective tube 70 from moving in an axial direction X with respect to the drive shaft 20. The protective-side first stopper 72 may be a ring-shaped member fixed to the outer peripheral surface of the distal portion of the protective tubular main body 71. The protective-side first stopper 72 has a protective-side distal surface 72A facing the distal direction and a protective-side proximal surface 72B facing the proximal direction. The normal line of the protective-side distal surface 72A has a component parallel to the axial direction X. The normal line of the protective-side proximal surface 72B has a component parallel to the axial direction X. The normal line being a vertical vector to the protective-side distal surface 72A and the protective-side proximal surface 72B that contacts a drive-side distal surface 46A or a drive-side proximal surface 46B.

Figure 5:
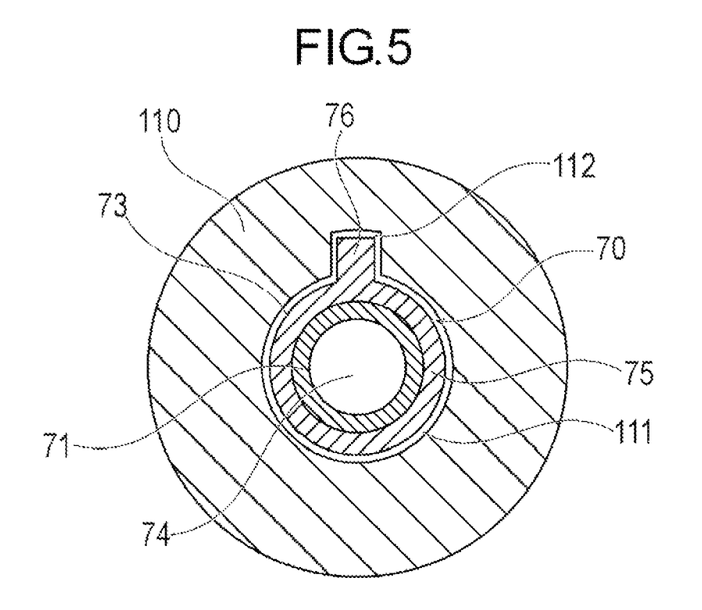
FIG. 5 is a cross-sectional view taken along line V-V of FIG. 4.

As illustrated in FIGS. 4 and 5, the protective-side second stopper 73 is fixed to the outer peripheral surface of the proximal portion of the protective tubular main body 71. Accordingly, the protective-side second stopper 73 rotates together with the protective tubular main body 71. The protective-side second stopper 73 helps prevent the protective tube 70 from rotating with respect to the handle 60. In accordance with an exemplary embodiment, the protective-side second stopper 73 has a circular tube-shaped fixed tube 75 fixed to the outer peripheral surface of the proximal portion of the protective tubular main body 71 and a protruding portion (protrusion) 76 protruding radially outward from a part of the outer peripheral surface of the fixed tube 75.

It is desirable that the material of the protective tubular main body 71 has a certain degree of flexibility and low friction. For example, the material of the protective tubular main body 71 can include polyetheretherketone (PEEK), a fluorine-based polymer such as PTFE and ETFE, polymethylmethacrylate (PMMA), polyethylene (PE), a polyether block acid copolymer (PEBAX), polyimide, and a combination of two or more of polyetheretherketone (PEEK), a fluorine-based polymer such as PTFE and ETFE, polymethylmethacrylate (PMMA), polyethylene (PE), a polyether block acid copolymer (PEBAX), and polyimide.

In accordance with an exemplary embodiment, the materials of the protective-side first stopper 72 and the protective-side second stopper 73 preferably have a certain degree of rigidity. Examples of the material of the protective-side first stopper 72 and the protective-side second stopper 73 preferably can include a material applicable to the main shaft 21 described above.

As illustrated in FIGS. 1 to 3, the cutting unit 40 is a member for cutting and reducing the size of an object such as plaque and a calcified lesion. Accordingly, "cutting" means reducing the size of the object by applying a force to the object in contact. Methods for applying the force during the cutting and the post-cutting shape and form of the object are not limited. The cutting unit 40 has a cutting distal portion 41 and a cutting proximal portion 42 disposed on the proximal side of the cutting distal portion 41.

The cutting distal portion 41 is positioned in the distal portion of the cutting unit 40 and has multiple minute or relatively small abrasive grains on a surface of the cutting distal portion 41 of the cutting unit 40. Alternatively, the cutting distal portion 41 may be provided with a sharp blade. The cutting distal portion 41 has a first through-hole 43 positioned on the distal side and a second through-hole 44 positioned on the proximal side of the first through-hole 43. The first through-hole 43 and the second through-hole 44 communicate with each other and penetrate the cutting distal portion 41 in the axial direction X. The ring-shaped protective-side first stopper 72 is rotatably disposed in the second through-hole 44. In accordance with an exemplary embodiment, the inner diameter of the first through-hole 43 is larger than the outer diameter of the protective tubular main body 71 and smaller than the outer diameter of the protective-side first stopper 72. Accordingly, the protective-side first stopper 72 can be prevented from entering the first through-hole 43 although the protective-side first stopper 72 can be positioned in the second through-hole 44.

The cutting proximal portion 42 is fitted into the proximal portion of the second through-hole 44 from the proximal side and is connected to the cutting distal portion 41. In accordance with an exemplary embodiment, the cutting proximal portion 42 has a third through-hole 45 extending along the axial direction X. The third through-hole 45 is positioned on the proximal side of the second through-hole 44 and communicates with the second through-hole 44. The inner diameter of the third through-hole 45 is larger than the outer diameter of the protective tubular main body 71 and smaller than the outer diameter of the protective-side first stopper 72. Accordingly, the protective-side first stopper 72 can be prevented from entering the third through-hole 45. The first through-hole 43, the second through-hole 44, and the third through-hole 45 are coaxially arranged in the axial direction X. An inner ring 81 of a bearing 80 is integrally formed in the proximal portion of the cutting proximal portion 42. In accordance with an exemplary embodiment, the bearing 80 can be a part of the cutting unit 40. It should be noted that the bearing 80 may be a configuration separate from the cutting unit 40.

The cutting unit 40 has a drive-side stopper 46 that comes into contact with the protective-side first stopper 72 and helps prevent the protective tube 70 from moving in the axial direction X. The drive-side stopper 46 has a drive-side distal surface 46A and a drive-side proximal surface 46B.

The drive-side distal surface 46A is formed in a step portion between the first through-hole 43 and the second through-hole 44 so as to face the proximal direction. The normal line of the drive-side distal surface 46A has a component parallel to the axial direction X (i.e., the normal line being a vertical vector to the protective-side distal surface 72A and the protective-side proximal surface 72B that contacts a drive-side distal surface 46A). In the present embodiment, the normal line of the drive-side distal surface 46A is parallel to the axial direction X. The drive-side distal surface 46A faces the protective-side distal surface 72A positioned in the second through-hole 44. The drive-side distal surface 46A is capable of smoothly sliding with the protective-side distal surface 72A while rotating relative to the protective-side distal surface 72A.

The drive-side proximal surface 46B is formed in the step portion between the second through-hole 44 and the third through-hole 45 so as to face the distal direction. The normal line of the drive-side proximal surface 46B has a component parallel to the axial direction X (i.e., the normal line being a vertical vector to the protective-side distal surface 72A and the protective-side proximal surface 72B that contacts a drive-side proximal surface 46B). In the present embodiment, the normal line of the drive-side proximal surface 46B is parallel to the axial direction X. The drive-side proximal surface 46B faces the protective-side proximal surface 72B positioned in the second through-hole 44. The drive-side proximal surface 46B is capable of smoothly sliding with the protective-side proximal surface 72B while rotating relative to the protective-side proximal surface 72B. In a state where the drive-side proximal surface 46B is in contact with the protective-side proximal surface 72B, the position of the most distal end of the protective tube 70 in the axial direction X coincides with a distal end opening surface 49 where a distal end opening portion 48 of the cutting unit 40 is formed or is closer to the distal side than the distal end opening surface 49. Accordingly, the most distal end of the protective tube 70 is not positioned closer to the proximal side than the distal end opening surface 49 even in a state of being positioned closest to the proximal side with respect to the cutting unit 40.

In accordance with an exemplary embodiment, a lubricant may be accommodated in the groove-shaped second through-hole 44. The lubricant may be, for example, silicone oil. As a result, with the use of a lubricant, slidability on the contact surface between the protective-side first stopper 72 and the drive-side stopper 46 can be improved.

In accordance with an exemplary embodiment, the outer peripheral surface of the cutting unit 40 has a notch portion 47 cut so as to have a substantially V shape in a cross section orthogonal to the axial direction X. The notch portion 47 functions as a flow path for transporting the cut object in the proximal direction. The notch portion 47 is disposed, for example, every 120 degrees in the circumferential direction. Accordingly, for example, the cutting unit 40 has three notch portions 47 evenly arranged in the circumferential direction. The edge portion of each notch portion 47 has a curvature and can be smoothly formed. It should be noted that the notch portion 47 is not limited to three in number.

The material of the cutting unit 40 is preferably strong enough to cut plaque, calcified lesions, and so on. The material of the cutting unit 40 can include, for example, stainless steel, nitinol, Ta, Ti, Pt, Au, W, brass, a shape memory alloy, and a super steel alloy. In accordance with an exemplary embodiment, in a case where a soft object such as a thrombus is to be cut, the material of the cutting unit 40 can include, for example, a fluorine-based polymer such as polytetrafluoroethylene (PTFE) and a tetrafluoroethylene-ethylene copolymer (ETFE), polyetheretherketone (PEEK), polyimide, a polyolefin such as polyethylene and polypropylene, polyamide, and polyester such as polyethylene terephthalate.

As illustrated in FIGS. 2 and 4, the outer tube 30 is a tubular body, which accommodates the drive shaft 20, the inner tube 50, and the protective tube 70. An aspiration lumen 31 may be formed between the outer tube 30 and the drive shaft 20 in order to aspirate the object, for example, plaque or a calcified lesion cut and reduced in size.

The outer tube 30 has an aspiration opening portion 33 at a distal end of the outer tube 30. The cut object or the liquid that has been released from the drive shaft 20 is aspirated in the aspiration opening portion 33. The distal end of the outer tube 30 is positioned near the proximal end of the cutting unit 40. The distal portion of the outer tube 30 is fixed to an outer ring 82 of the bearing 80 to be described later. The outer tube 30 has a proximal end opening portion 35 that opens in the handle 60 at a proximal end of the outer tube 30.

An anti-kink protector 32 and an operation unit 68 can be fixed to the outer peripheral surface of the proximal portion of the outer tube 30. The anti-kink protector 32 suppresses a kink on the proximal side of the outer tube 30. An aspiration seal portion 92, which will be described later, is in contact with the outer surface of the outer tube 30 that is closer to the proximal side than the site connected to the operation unit 68.

The material of outer tube 30 preferably has a certain degree of strength. For example, the material of the outer tube 30 can include stainless steel, nitinol, Ta, Ti, Pt, Au, W, a shape memory alloy, engineering plastics such as ABS resin, polycarbonate (PC), polymethylmethacrylate (PMMA), polyacetal (POM), polyphenylsulfone (PPSU), polyethylene (PE), a carbon fiber, and polyetheretherketone (PEEK), and a combination of two or more of stainless steel, nitinol, Ta, Ti, Pt, Au, W, a shape memory alloy, engineering plastics such as ABS resin, polycarbonate (PC), polymethylmethacrylate (PMMA), polyacetal (POM), polyphenylsulfone (PPSU), polyethylene (PE), a carbon fiber, and polyetheretherketone (PEEK).

In accordance with an exemplary embodiment, the bearing 80 is capable of securing a space between the inner ring 81 and the outer ring 82 so that a fluid such as a liquid and a gas or the size-reduced object such as plaque and a calcified lesion can be circulated. The bearing 80 includes the tubular inner ring 81, the tubular outer ring 82 disposed so as to surround the inner ring 81, and a plurality of rolling bodies 83 disposed between the inner ring 81 and the outer ring 82. The inner ring 81 is rotatably supported by the outer ring 82 via the rolling body 83. The inner ring 81 and the outer ring 82 are relatively rotatable about the shaft center. The outer ring 82 is fixed to the distal portion of the outer tube 30. The inner ring 81 is fixed to the proximal end of the cutting unit 40. It should be noted that the inner ring 81 may be a part of the cutting unit 40. In addition, the outer ring 82 may be a part of the outer tube 30.

The inner tube 50 is a flexible tubular body surrounding the drive shaft 20 and in the outer tube 30. In accordance with an exemplary embodiment, the distal end of the inner tube 50 is positioned closer to the proximal side than the distal end of the drive shaft 20. The proximal end of the inner tube 50 may be fixed to the handle 60. A liquid delivering lumen 51 delivering a liquid in the distal direction is formed between the inner tube 50 and the drive shaft 20. It should be noted that the drive shaft 20 positioned inside the inner tube 50 is capable of passing a liquid between the inner peripheral surface and the outer peripheral surface via the gaps between the wire rods as constituent materials. Accordingly, the gaps between the drive shaft 20 and the protective tube 70 also functions as the liquid delivering lumen 51. In the outer tube 30, the liquid delivering lumen 51 is positioned inside the inner tube 50 and the aspiration lumen 31 is positioned outside the inner tube 50. The inner tube 50 suppresses fluid leakage from the liquid delivering lumen 51 to the aspiration lumen 31 and effectively transmits the liquid delivering pressure and the aspiration pressure of the handle 60 to the distal side of the inner tube 50.

In accordance with an exemplary embodiment, the material of the inner tube 50 has a certain degree of flexibility and low friction. For example, the material of the inner tube 50 can be polyetheretherketone (PEEK), a fluorine-based polymer such as PTFE and ETFE, polymethylmethacrylate (PMMA), polyethylene (PE), a polyether block acid copolymer (PEBAX), polyimide, and a combination of two or more of polyetheretherketone (PEEK), a fluorine-based polymer such as PTFE and ETFE, polymethylmethacrylate (PMMA), polyethylene (PE), a polyether block acid copolymer (PEBAX), polyimide.

As illustrated in FIGS. 1, 4, and 5, the handle 60 includes a casing 61, the drive unit 62, a switch 63, a liquid delivering port 64, an aspiration port 65, and an electric cable 66. The handle 60 further includes the operation unit 68, an aspiration unit 90, a liquid delivering portion 100, and a handle-side stopper 110.

In accordance with an exemplary embodiment, the casing 61 accommodates the drive unit 62, the liquid delivering portion 100, and the aspiration unit 90. A bearing-shaped first support portion 67 rotatably supporting the operation unit 68 is formed in the distal portion of the casing 61.

The drive unit 62 can be, for example, a hollow motor (i.e., hollow shaft motor). The drive unit 62 is rotated by electric power supplied from the outside via the electric cable 66. The drive tube 22 of the drive shaft 20 penetrates the drive unit 62. The drive tube 22 is directly connected to the hollow drive rotor 62A of the hollow motor. Although the rotation speed of the drive unit 62 is not particularly limited, the speed can be, for example, 5,000 revolutions per minute (rpm) to 200,000 rpm. It should be noted that the configuration of the drive unit 62 is not particularly limited.

The electric cable 66 can be connected to an external power source or control device. The switch 63 is where an operator drives and stops the drive unit 62.

The operation unit 68 is where the operator performs operation with his or her finger to apply a rotational torque to the outer tube 30. The operation unit 68 is rotatable with respect to the casing 61. The operation unit 68 is fixed to the outer peripheral surface of the proximal portion of the outer tube 30.

The liquid delivering port 64 can be connected to a liquid delivering source 11 such as, for example, an external liquid delivering pump. The liquid delivering port 64 is supplied with a liquid such as a saline solution that is delivered into the living body from the liquid delivering source 11. The liquid delivering port 64 transports the supplied liquid to the liquid delivering portion 100. For example, a pump, a bag suspended from a drip tower, and a syringe can be used as the liquid delivering source 11 insofar as a liquid delivering pressure can be generated. The amount of liquid delivery can be stabilized by using the liquid delivering source 11 that is capable of delivering a liquid actively, for example, a pump.

The aspiration port 65 can be connected to an aspiration source 12 such as an external aspiration pump. The aspiration port 65 is aspirated by the aspiration source 12 and transports, for example, the liquid in the aspiration unit 90 toward the aspiration source 12. A pump, a syringe, or the like can be used as the aspiration source 12 insofar as it is capable of generating an aspiration pressure. It is possible to achieve an increase in aspiration pressure and aspiration force stabilization and improvement by using the aspiration source 12 that is capable of active aspiration, for example, by use of a pump.

The aspiration unit 90 is where the aspiration pressure is applied to the aspiration lumen 31 of the outer tube 30. The aspiration unit 90 includes a first housing 91 and the aspiration seal portion 92.

The first housing 91 includes an aspiration port 94 where a liquid is released to the outside of the handle 60 and a first space portion 95 communicating with the aspiration port 94. The proximal end opening portion 35 of the outer tube 30 is positioned in the first space portion 95. The inner tube 50 is fixed to the proximal portion of the first space portion 95. The aspiration port 94 is connected to the aspiration port 65.

The aspiration seal portion 92 is positioned between the first housing 91 and the outer tube 30 in the distal portion of the first space portion 95. The aspiration seal portion 92 suppresses an external air flow into the first space portion 95. Further, the aspiration seal portion 92 rotatably supports the outer tube 30.

The liquid delivering portion 100 is positioned on the proximal side of the aspiration unit 90 and the distal side of the drive unit 62. The liquid delivering portion 100 is where a liquid is sent to the liquid delivering lumen 51 and the guide wire lumen 74. The liquid delivering portion 100 includes a second housing 101, a liquid delivering seal portion 103, and a fixing member 106.

The second housing 101 includes a liquid delivering port 104 to which a liquid is delivered from outside of the handle 60 and a second space portion 105 communicating with the liquid delivering port 104. The drive shaft 20 penetrates the second space portion 105. The side hole 77 passing a liquid to the guide wire lumen 74 is positioned in the second space portion 105. The liquid delivering port 104 is connected to the liquid delivering port 64.

The liquid delivering seal portion 103 can be positioned between the second housing 101 and the drive tube 22 of the drive shaft 20 in the proximal portion of the second space portion 105. The liquid delivering seal 103 helps suppress an outflow of the pressurized liquid in the second space portion 105. The fixing member 106 is a tubular member fixing the liquid delivering seal 103 to the second housing 101.

The handle-side stopper 110 helps prevent the protective tube 70 from rotating with respect to the handle 60. The handle-side stopper 110 is fixed to the proximal portion of the casing 61. The handle-side stopper 110 has a sliding hole 111 larger in inner diameter than the outer peripheral surface of the fixed tube 75 and a holding portion 112 disposed on a part of the inner peripheral surface of the sliding hole 111.

The holding portion 112 can be a groove extending in the axial direction X. The holding portion 112 sandwiches both sides of the protruding portion 76 in the circumferential direction. The protruding portion 76 can be held by the holding portion 112 so as to be slidable in the axial direction X. It should be noted that the holding portion 112 may not be a groove insofar as the protruding portion 76 can be held so as to be slidable in the axial direction X. For example, the holding portion 112 may be a projecting portion sandwiching both sides of the protruding portion 76 in the circumferential direction. The inner diameter of the sliding hole 111 is smaller than the distance (radius) from the central axis of the protective tube 70 to the top portion of the protruding portion 76. Accordingly, the protruding portion 76 accommodated in the holding portion 112 is prevented from entering the sliding hole 111 and is held in the holding portion 112. Accordingly, the handle-side stopper 110 prevents the protective tube 70 from rotating with respect to the handle 60 while allowing the protective tube 70 to move in the axial direction X with respect to the handle 60. A lubricant may be accommodated in the sliding hole 111 and the holding portion 112. The lubricant can be, for example, silicone oil. As a result, it is possible to improve slidability on the contact surface between the protective-side second stopper 73 and the handle-side stopper 110 can be improved with the use of a lubricant.

Next, a method for using the medical device 10 according to the present embodiment will be described by taking as an example a case where a lesion area such as plaque and a calcified lesion in a blood vessel is cut and aspirated.

Figure 6:
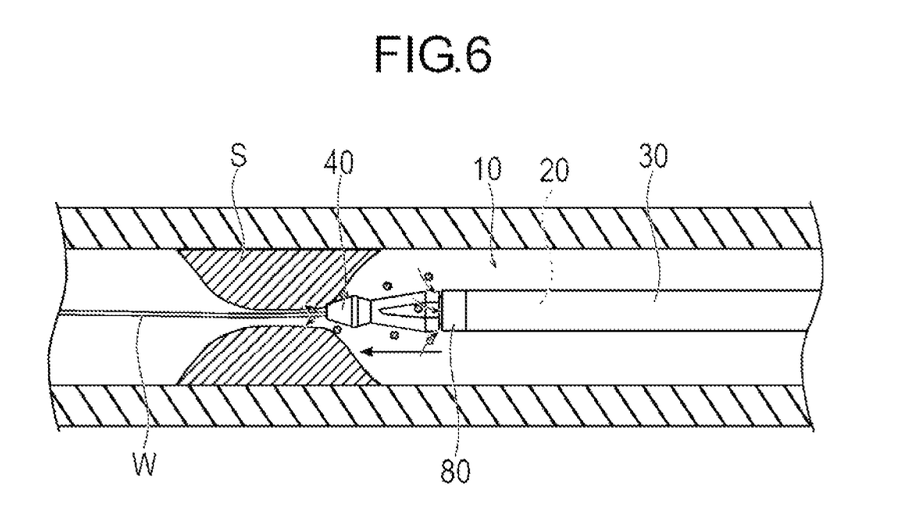
FIG. 6 is a schematic view illustrating a state where the medical device performs cutting.

First, an operator inserts a guide wire W into the blood vessel to reach the vicinity of a lesion area S. Next, the operator inserts the proximal end of the guide wire W into the guide wire lumen 74 of the medical device 10. Subsequently, the operator moves the cutting unit 40 to the vicinity of the lesion area S by using the guide wire W as a guide as illustrated in FIG. 6.

Next, the operator operates the switch 63 to initiate liquid delivery and aspiration as illustrated in FIGS. 1, 2, and 4. In other words, the operator operates the external liquid delivering source 11 and the aspiration source 12. The cutting unit 40 is rotated via the drive shaft 20 at the same time or after the passage of a certain period of time. As a result, the operator can cut the lesion area S with the cutting unit 40.

The operator can operate the operation unit 68 in a case where he or she wishes to change the position of the cutting unit 40 in the circumferential direction. When the operator rotates the operation unit 68, the operation unit 68 supported by the first support portion 67 rotates. As a result, the operator can change the position of the cutting unit 40 in the blood vessel. The distal portion of the medical device 10, that is, the distal portion of the outer tube 30 may be formed so as to be bent in advance. In case where the distal portion of the outer tube 30 is bent in advance, the operator can effectively change the position of the cutting unit 40 in the blood vessel by rotating the operation unit 68 to change the direction of the distal portion of the outer tube 30. In a case where the distal portion of the medical device 10 is bent, the protective tubular main body 71 disposed in the outer tube 30 may also be in a shape that matches the shape in which the outer tube 30 is bent in advance. As a result, the friction between the drive shaft 20 bent in the outer tube 30 and the bent protective tubular main body 71 can be reduced. In addition, the outer peripheral edge portions of the distal and proximal ends of the protective tubular main body 71 may be smoothly treated so as to have a curvature.

In addition, the operator can cause the outer tube 30 to reciprocate along the direction of elongation of the blood vessel by moving the entire handle 60 or the outer tube 30 exposed to the outside of the living body. As a result, the operator can cut the lesion area S along the direction of elongation of the blood vessel with the cutting unit 40.

After the liquid delivery is initiated, the saline solution that has flowed into the second space portion 105 from the liquid delivering port 104 enters the liquid delivering lumen 51 inside the inner tube 50. Further, the saline solution that has flowed into the second space portion 105 flows into the drive shaft 20 through the gap between the wire rods of the drive shaft 20. The saline solution that has flowed into the drive shaft 20 flows into the lumen between the drive shaft 20 and the protective tube 70 (a part of the liquid delivering lumen 51) and flows from the side hole 77 into the guide wire lumen 74 inside the protective tube 70. It should be noted that the space between the drive shaft 20 and the second housing 101 is sealed by the liquid delivering seal 103.

The saline solution that has entered the liquid delivering lumen 51 and the guide wire lumen 74 moves in the distal direction. After the saline solution in the liquid delivering lumen 51 reaches the distal side from the inner tube 50, the saline solution moves to the aspiration lumen 31.

In accordance with an exemplary embodiment, the saline solution in the guide wire lumen 74 can be released in part into the blood vessel from the distal end opening portion 48. The saline solution that has entered the blood vessel is partially aspirated into the aspiration lumen 31 of the outer tube 30 together with the blood and the cut object. It should be noted that the saline solution in the guide wire lumen 74 may not be released into the blood vessel from the distal end opening portion 48. The object and the liquid that have entered the aspiration lumen 31 move the aspiration lumen 31 to the proximal side. As illustrated in FIG. 2, the liquid that has entered the aspiration lumen 31 is diluted by the saline solution merging from the liquid delivering lumen 51 on the distal side of the inner tube 50. Accordingly, thrombus formation in the aspiration lumen 31 can be suppressed and the amount of aspiration by lowering the viscosity of the aspirated material can be increase. After the liquid that has entered the aspiration lumen 31 reaches the first space portion 95 of the aspiration unit 90, the liquid is released from the aspiration port 94 to the external aspiration source 12. In accordance with an exemplary embodiment, the aspiration pressure at this time can be, for example, 0 kPa to 90 kPa, and preferably 0 kPa to 50 kPa when the absolute vacuum is 0 kPa.

In accordance with an exemplary embodiment, the position of the most distal end of the protective tube 70 is appropriately maintained by the protective-side first stopper 72 disposed in the distal portion of the protective tube 70 and the drive-side stopper 46 disposed at the cutting unit 40. For example, when the medical device 10 is bent in the blood vessel, the protective tube 70 positioned substantially at the center of the medical device 10 may tend to protrude in the distal direction from the distal end opening surface 49 of the cutting unit 40. In addition, the protective tube 70 may tend to protrude in the distal direction from the distal end opening surface 49 due to the force that is received from the fluid flowing in the distal direction through the liquid delivering lumen 51. When the distal portion of the protective tubular main body 71 moves in the distal direction with respect to the drive shaft 20 and the cutting unit 40, the protective-side distal surface 72A comes into contact with the drive-side distal surface 46A. Accordingly, an excessive protrusion of the most distal end of the protective tubular main body 71 from the distal end opening surface 49 of the cutting unit 40 can be suppressed. An excessive protrusion of the protective tubular main body 71 from the distal end opening surface 49 is likely to result in contact between the protruding protective tubular main body 71 and the lesion area S to be cut. As a result, contact between the cutting unit 40 and the lesion area S may be hindered by the protective tubular main body 71. In addition, the protruding protective tubular main body 71 may be kinked. The pushing performance of the cutting unit 40 with respect to a narrow body lumen may also be lowered by the protruding protective tubular main body 71. In contrast, in the present embodiment, the protective tubular main body 71 does not excessively protrude from the distal end opening surface 49, and thus the protective tubular main body 71 does not hinder the contact of the cutting unit 40 with the lesion area S to be cut. Accordingly, the cutting unit 40 is capable of maintaining an appropriate cutting force. In addition, the kinking of the protruding protective tubular main body 71 can be suppressed. In addition, it is possible to suppress the pushing performance of the cutting unit 40 with respect to a narrow body lumen being lowered by the protective tubular main body 71 protruding from the distal end opening surface 49.

In accordance with an exemplary embodiment, the protective-side proximal surface 72B comes into contact with the drive-side proximal surface 46B when the distal portion of the protective tube 70 moves in the proximal direction with respect to the drive shaft 20 and the cutting unit 40. Accordingly, a movement of the most distal end of the protective tubular main body 71 to the proximal side beyond the distal end opening surface 49 of the cutting unit 40 can be suppressed. Accordingly, the protective tube 70 can hinder or help prevent the contact of the guide wire W with the rotating cutting unit 40 or the inner peripheral surface of the drive shaft (edge portion of a distal side opening portion 78 of the cutting unit 40 in particular). Accordingly, breakage of the guide wire W and coating peeling can be suppressed.

As described above, the protective-side first stopper 72 and the drive-side stopper 46 restrain the distal portion of the protective tube 70 from moving in the axial direction X with respect to the cutting unit 40 and the drive shaft 20. However, the protective-side first stopper 72 and the drive-side stopper 46 do not prevent rotation. Accordingly, the protective tube 70 is capable of rotating relative to the cutting unit 40 and the drive shaft 20 without hindering the rotation of the rotating cutting unit 40 and drive shaft 20.

Further, the rotation of the protruding portion 76 of the protective-side first stopper 72 positioned in the proximal portion of the protective tube 70 can be prevented by the holding portion 112 of the handle-side stopper 110 disposed in the handle 60. Accordingly, a following rotation of the protective tube 70 can be suppressed by the frictional force between the rotating drive shaft 20 and cutting unit 40. It should be noted that the protruding portion 76 is capable of freely moving in the axial direction X in the holding portion 112. Accordingly, in the event of a deviation in the lengths of the protective tube 70 and the drive shaft 20 in the axial direction X attributable to, for example, the medical device 10 bending in the blood vessel, the protruding portion 76 moves in the axial direction X in the holding portion 112 and it is possible to escape from the length deviation. In a case where it is impossible to escape from this length deviation, the protective tube 70 is curved (in, for example, a bellows shape) in the drive shaft 20 and the cutting unit 40. As a result, the friction between the inner peripheral surfaces of the drive shaft 20 and the cutting unit 40 and the outer peripheral surface of the protective tube 70 increases and the guide wire W inserted into the protective tube 70 is twisted. In contrast, in the present embodiment, it is possible to escape from the length deviation. Accordingly, the protective tube 70 is not curved in the drive shaft 20 and the cutting unit 40 and it is possible to suppress an increase in the friction between the inner peripheral surfaces of the drive shaft 20 and the cutting unit 40 and the outer peripheral surface of the protective tube 70. Accordingly, the twisting of the guide wire W inserted into the protective tube 70 can be suppressed.

In accordance with an exemplary embodiment, the operator presses the switch 63 after the cutting and aspiration of the lesion area S is completed. As a result, the rotation of the drive shaft 20 is stopped and the cutting by the cutting unit 40 is stopped. The liquid delivery and aspiration is stopped at the same time or after the passage of a certain period of time. In other words, the external liquid delivering source 11 and the aspiration source 12 are stopped. Subsequently, the medical device 10 is removed from the blood vessel and the treatment is completed.

As described above, the medical device 10 according to the present embodiment, which is the medical device 10 that cuts an object in a body lumen, has the rotatable and tubular drive shaft 20, the cutting unit 40 fixed to the distal portion of the drive shaft 20 and having a through-hole communicating with the lumen of the drive shaft 20, the protective tubular main body 71 accommodated in the drive shaft 20 and the cutting unit 40 and rotatable relative to the drive shaft 20, the handle 60 rotatably holding the proximal portion of the drive shaft 20, and the protective-side first stopper 72 as a projecting portion or recessed portion (projection or recess) disposed on (or in) the outer peripheral surface of the distal portion of the protective tubular main body 71. The distal portion of the drive shaft 20 or the cutting unit 40 includes the drive-side stopper 46 contactable with the protective-side first stopper 72. By the protective-side first stopper 72 coming into contact with the drive-side stopper 46, the protective tubular main body 71 is prevented from moving axially with respect to the drive shaft 20 without being prevented from rotating relative to the drive shaft 20.

In accordance with an exemplary embodiment, the medical device 10 configured as described above is capable of suppressing an excessive movement of the protective tubular main body 71 in the axial direction (distal and/or proximal direction) with respect to the cutting unit 40. Accordingly, the protective tubular main body 71 is capable of appropriately protecting the guide wire W inserted into the drive shaft 20 and the cutting unit 40. In a case where the protective tubular main body 71 is prevented from moving in the proximal direction with respect to the cutting unit 40, it is possible to suppress an excessive proximal movement of the protective tubular main body 71 with respect to the cutting unit 40. Accordingly, contact between the rotating cutting unit 40 and the guide wire W passed through the protective tubular main body 71 can be suppressed. As a result, breakage of the guide wire W, coating peeling, and so on can be suppressed. In a case where the protective tubular main body 71 is prevented from moving in the distal direction with respect to the cutting unit 40, it is possible to suppress an excessive distal protrusion of the guide wire W passed through the protective tubular main body 71 beyond the cutting unit 40. As a result, the protective tubular main body 71 does not hinder contact between the cutting unit 40 and the cutting target and the cutting force can be appropriately maintained. In addition, it is possible to suppress a decline in the pushing performance of the medical device 10 with respect to a narrow body lumen. In addition, the medical device 10 has the protective tubular main body 71 in the drive shaft 20, and thus the friction between the drive shaft 20 and the guide wire W can be reduced.

In addition, the protective-side first stopper 72 has the protective-side proximal surface 72B facing the proximal direction and the drive-side stopper 46 has the drive-side proximal surface 46B facing the distal direction and facing the protective-side proximal surface 72B on the proximal side of the protective-side proximal surface 72B. By the protective tubular main body 71 moving in the proximal direction with respect to the drive shaft 20 and the protective-side proximal surface 72B coming into contact with the drive-side proximal surface 46B, the protective tubular main body 71 is prevented from moving in the proximal direction with respect to the drive shaft 20 without being restrained from rotating relative to the drive shaft 20. As a result, it is possible to suppress an excessive proximal movement of the protective tubular main body 71 with respect to the cutting unit 40. Accordingly, breakage of the guide wire W passed through the protective tubular main body 71, coating peeling, and so on can be suppressed.

In addition, in a state where the protective-side proximal surface 72B is in contact with the drive-side proximal surface 46B, the position of the most distal end of the protective tubular main body 71 in the axial direction X coincides with the position of the most distal end of the cutting unit 40 or is closer to the distal side than the most distal end of the cutting unit 40. As a result, the guide wire W passing through the protective tubular main body 71 can be reliably prevented from coming into contact with the rotating cutting unit 40 and breakage of the guide wire W and coating peeling can be reliably suppressed.

In addition, the protective-side first stopper 72 has the protective-side distal surface 72A facing the distal direction and the drive-side stopper 46 has the drive-side distal surface 46A facing the proximal direction and facing the protective-side distal surface 72A on the distal side of the protective-side distal surface 72A. By the protective tubular main body 71 moving in the distal direction with respect to the drive shaft 20 and the protective-side distal surface 72A coming into contact with the drive-side distal surface 46A, the protective tubular main body 71 is prevented from moving in the distal direction with respect to the drive shaft 20 without being restrained from rotating relative to the drive shaft 20. As a result, it is possible to suppress an excessive distal movement of the protective tubular main body 71 with respect to the cutting unit 40. Accordingly, the protective tubular main body 71 does not hinder contact between the cutting unit 40 and the cutting target and the cutting force can be appropriately maintained.

In addition, the handle 60 has the handle-side stopper 110 restraining the protective tubular main body 71 from rotating. As a result, the handle-side stopper 110 is capable of suppressing the rotation of the protective tubular main body 71 that is attributable to the frictional force received from the rotating drive shaft 20. Accordingly, the guide wire W inserted into the protective tubular main body 71 is unlikely to be affected by rotation from the drive shaft 20 and the cutting unit 40.

In addition, the handle-side stopper 110 allows the protective tubular main body 71 to move in the axial direction X of the handle 60. As a result, it is possible to escape from the deviation in the lengths of the protective tubular main body 71 and the drive shaft 20 in the axial direction X that is attributable to, for example, the medical device 10 bending in the body lumen. Accordingly, the protective tubular main body 71 is not curved in the drive shaft 20 and the cutting unit 40 and it is possible to suppress an increase in the friction between the inner peripheral surfaces of the drive shaft 20 and the cutting unit 40 and the outer peripheral surface of the protective tubular main body 71. Accordingly, the twisting of the guide wire W inserted into the protective tubular main body 71 can be suppressed.

In addition, the protruding portion 76 protruding in the circumferential direction is disposed on the outer peripheral surface of the protective tubular main body 71, the handle-side stopper 110 has the holding portion 112 sandwiching the protruding portion 76 in the circumferential direction, and the holding portion 112 prevents the protective tubular main body 71 and the handle-side stopper 110 from rotating relative to each other and allows the protective tubular main body 71 and the handle-side stopper 110 to move relative to each other in the axial direction X. As a result, it is possible to rather easily realize a structure in which the protective tubular main body 71 does not rotate while moving in the axial direction X with respect to the handle 60. The protruding portion 76 disposed on the outer peripheral surface of the protective tubular main body 71 may be a structure integrated with the protective tubular main body 71 or a structure separate from the protective tubular main body 71.

In addition, the handle-side stopper 110 may have a protruding portion in the circumferential direction, a holding portion sandwiching the protruding portion in the circumferential direction may be disposed on the outer peripheral surface of the protective tubular main body 71, and the holding portion may be configured to restrain the protective tubular main body 71 and the handle-side stopper 110 from rotating relative to each other and allow the protective tubular main body 71 and the handle-side stopper 110 to move relative to each other in the axial direction X. Even with such a configuration, it is possible to rather easily realize a structure in which the protective tubular main body 71 does not rotate while moving in the axial direction X with respect to the handle 60. The holding portion disposed on the outer peripheral surface of the protective tubular main body 71 may be a structure integrated with the protective tubular main body 71 or a structure separate from the protective tubular main body 71.

In addition, the handle 60 has the liquid delivering port 104 where a liquid is delivered from outside of the handle 60 and the liquid delivering port 104 communicates with the space between the protective tubular main body 71 and the drive shaft 20 and/or the inside of the protective tubular main body 71. As a result, the protective tubular main body 71 receives a force in the distal direction from the liquid that comes into contact with the outside surface and/or the inside surface of the protective tubular main body 71. However, an excessive movement of the protective tubular main body 71 in the distal and/or proximal direction with respect to the cutting unit 40 may be suppressed, and thus the impact of the fluid on the protective tubular main body 71 can be reduced.

It should be noted that the disclosure is not limited to the embodiment described above and various modifications can be made by those skilled in the art within the technical idea of the present disclosure. For example, the body lumen into which the medical device 10 is inserted is not limited to a blood vessel and may be a vessel, a ureter, a bile duct, an oviduct, a hepatic duct, and so on.

In addition, although the protective-side first stopper 72 is a ring-shaped projecting portion disposed over 360 degrees on the outer peripheral surface of the protective tubular main body 71 in the embodiment described above, the protective-side first stopper 72 may be a projecting portion of less than 360 degrees (projecting portion where the protective-side distal surface 72A and the protective-side proximal surface 72B are partially missing). In addition, although the drive-side stopper 46 is a groove-shaped recessed portion disposed over 360 degrees in the inner peripheral surface of the drive shaft 20, the drive-side stopper 46 may be a recessed portion of less than 360 degrees (recessed portion where the drive-side distal surface 46A and the drive-side proximal surface 46B are partially missing).

In addition, although the protective-side first stopper 72 is disposed with a ring-shaped projecting portion on the outer peripheral surface of the protective tubular main body 71 and the drive-side stopper 46 is formed by a groove-shaped recessed portion in the inner peripheral surface of the drive shaft 20 in the embodiment described above, the configuration may be reversed. For example, the protective-side first stopper 72 may be disposed with a groove-shaped recessed portion in the outer peripheral surface of the protective tubular main body 71 and the drive-side stopper 46 may be formed by a ring-shaped projecting portion on the inner peripheral surface of the drive shaft 20.

Figure 7A:
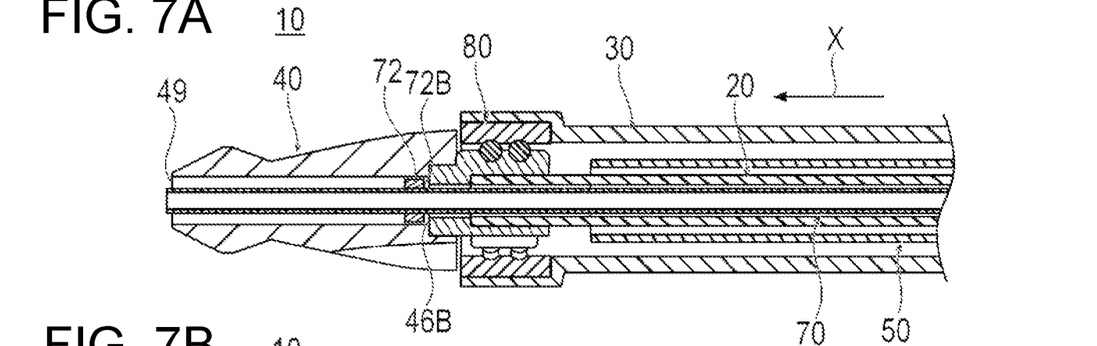

In addition, the medical device 10 may lack the protective-side distal surface 72A and the drive-side distal surface 46A as in a first modification example illustrated in FIG. 7A. Even with such a configuration, the protective-side proximal surface 72B and the drive-side proximal surface 46B are capable of preventing a proximal movement of the most distal end of the protective tube 70 beyond the distal end opening surface 49 of the cutting unit 40.

Figure 7B:
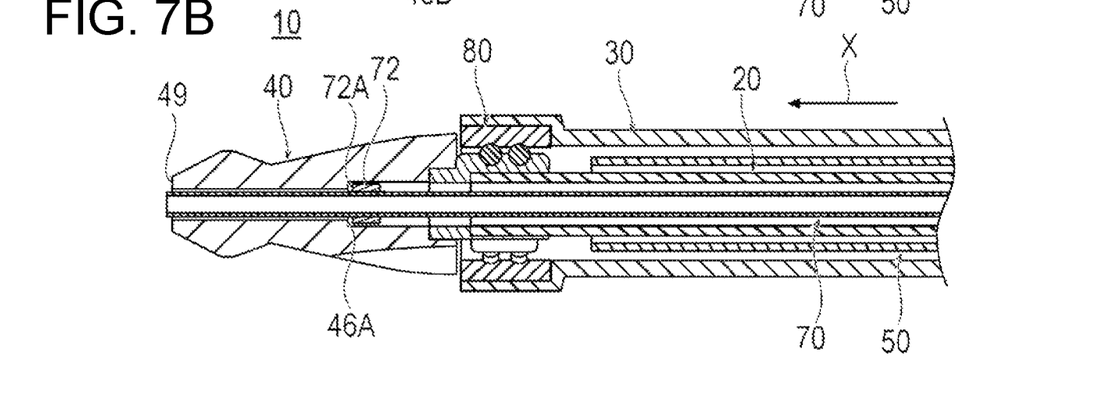

In addition, the medical device 10 may lack the protective-side proximal surface 72B and the drive-side proximal surface 46B as in a second modification example illustrated in FIG. 7B. Even with such a configuration, the protective-side distal surface 72A and the drive-side distal surface 46A are capable of suppressing an excessive protrusion of the most distal end of the protective tube 70 from the distal end opening surface 49 of the cutting unit 40. When the protective tube 70 moves to the proximal side in such a configuration, the most distal end of the protective tube 70 is capable of moving to the proximal side beyond the distal end opening surface 49 of the cutting unit 40. It should be noted that the guide wire W and the cutting unit 40 preferably do not come into direct contact with each other although not limited. For example, even in a state where the most distal end of the protective tube 70 is positioned closer to the proximal side than the distal end opening surface 49 by a relatively small length (for example, such as approximately 1 mm), breakage of the guide wire W passed through the protective tube 70, coating peeling, and so on can be prevented unless the protective tube 70 and the guide wire W come into direct contact with each other. In addition, the inner peripheral surface of the distal end of the cutting unit 40 may be opened so as to expand toward the distal side (for example, in a tapered shape). In this case, contact between the cutting unit 40 and the guide wire W passed through the protective tube 70 can be prevented even with the most distal end of the protective tube 70 positioned closer to the proximal side than the distal end opening surface 49.

In addition, although the handle-side stopper 110 has the recessed holding portion 112 in the inner peripheral surface and the protective-side second stopper 73 is formed on the outer peripheral surface of the protective tube 70 in the embodiment described above, the configuration may be reversed. For example, the recessed holding portion 112 may be formed in the protective-side second stopper 73 and the protruding portion 76 held by the holding portion 112 may be formed on the handle-side stopper 110.

Figure 8:
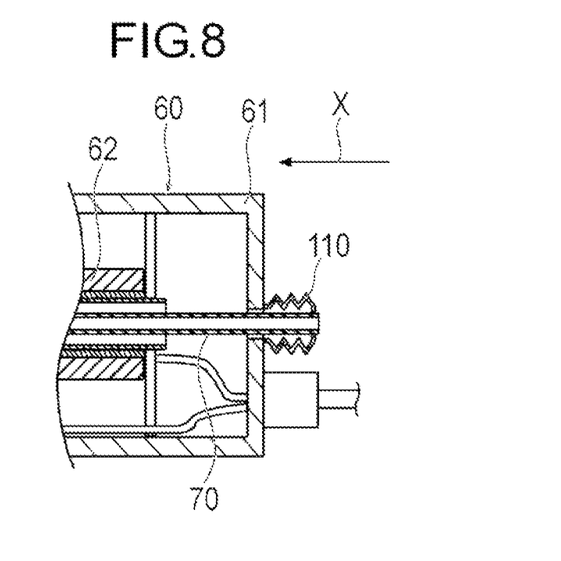
FIG. 8 is a cross-sectional view illustrating the proximal portion of the medical device according to a third modification example.

In addition, the form of the handle-side stopper 110 is not particularly limited insofar as it is possible to restrain the protective tube 70 from rotating with respect to the handle 60 while allowing the protective tube 70 to move in the axial direction X with respect to the handle 60. For example, as in a third modification example illustrated in FIG. 8, the handle-side stopper 110 may be a member telescopic in the axial direction X and yet resistant to twisting. The handle-side stopper 110 can be, for example, a bellows-shaped member, a spring member, or a coil. One end portion of the handle-side stopper 110 is fixed to the casing 61, and the other end portion of the handle-side stopper 110 is fixed to the protective tube 70. As a result, the protective tube 70 is capable of moving in the axial direction X with respect to the handle 60 by the handle-side stopper 110 being telescopic. Further, the protective tube 70 is restrained from rotating with respect to the handle 60 by being fixed to the casing 61 via the handle-side stopper 110 that is resistant to twisting.

In addition, at least one of the handle-side stopper 110 and the protective-side second stopper 73 may be rather easily deformed. Examples of the rather easily deformable materials that can be used for at least one of the handle-side stopper 110 and the protective-side second stopper 73 can include various rubber materials such as natural rubber, silicone rubber, butyl rubber, isoprene rubber, butadiene rubber, and styrene-butadiene rubber, various thermoplastic elastomers such as polyurethane-based, polyester-based, polyamide-based, olefin-based, and styrene-based, and highly elastic materials such as mixtures of two or more of natural rubber, silicone rubber, butyl rubber, isoprene rubber, butadiene rubber, and styrene-butadiene rubber, various thermoplastic elastomers such as polyurethane-based, polyester-based, polyamide-based, olefin-based, and styrene-based. When a sharp (peaky) torque acts on the protective tube 70 in this case, for example, the handle-side stopper 110 receives a force from the protective-side second stopper 73 and at least one of the handle-side stopper 110 and the protective-side second stopper 73 is deformed. As a result, at least one of the handle-side stopper 110 and the protective-side second stopper 73 is capable of absorbing the torque. Accordingly, damage to the protective tube 70 and the handle 60 can be prevented. In addition, at least one of the handle-side stopper 110 and the protective-side second stopper 73 may be fragile. When a sharp (peaky) torque acts on the protective tube 70 in this case, for example, the handle-side stopper 110 receives a force from the protective-side second stopper 73 and at least one of the handle-side stopper 110 and the protective-side second stopper 73 is broken. As a result, at least one of the handle-side stopper 110 and the protective-side second stopper 73 is capable of absorbing the torque. Accordingly, damage to the site of the medical device 10 other than the handle-side stopper 110 and the protective-side second stopper 73 can be prevented.

In addition, the aspiration port 94 of the aspiration unit 90 may be opened to atmospheric pressure without being connected to the aspiration source 12. Even with such a configuration, the aspiration unit 90 is capable of aspirating the object in the body lumen in a case where the pressure in the body lumen is higher than the atmospheric pressure.

In addition, the proximal portion of the protective tube 70 may be fixed to the handle 60 so as to be incapable of rotating and/or incapable of moving in the axial direction X.

In addition, the medical device 10 may lack a liquid delivering structure or a liquid aspiration structure.

Figure 9A:
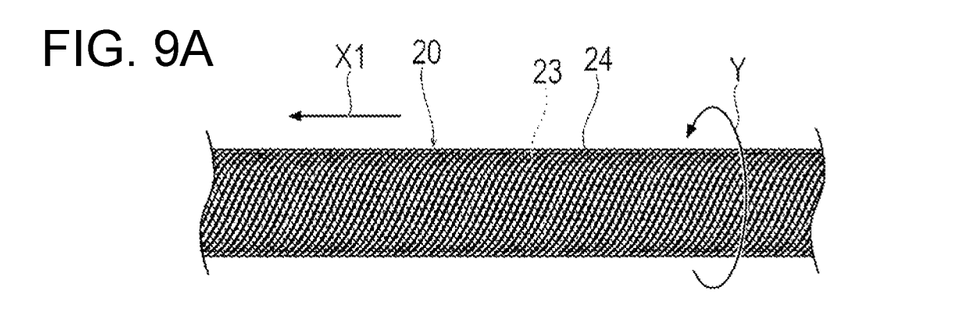

In addition, the drive shaft 20 may be a two-layer structure having an inner first layer 23 and an outer second layer 24 as in a fourth modification example illustrated in FIG. 9A. In accordance with an exemplary embodiment, the first layer 23 includes a plurality of wire rods wound in the forward direction of a rotation direction Y of the drive shaft 20 toward a distal direction X1. It should be noted that the first layer 23 may be formed by one wire rod although the first layer 23 is preferably formed by a plurality of wire rods. The second layer 24 surrounds the outside of the first layer 23. The second layer 24 includes a plurality of wire rods wound in the direction opposite to the rotation direction Y toward the distal direction X1. It should be noted that the second layer 24 may be formed by one wire rod although the second layer 24 is preferably formed by a plurality of wire rods. When torque acts on the drive shaft 20, the wire rod of the first layer 23 receives a force such that the winding loosens. Accordingly, the first layer 23 expands in the radial direction. In addition, the torque acting on the drive shaft 20 causes the wire rod of the second layer 24 to receive a force such that the winding becomes tight. Accordingly, the second layer 24 contracts in the radial direction and holds the winding-loosening first layer 23 from the outside. Accordingly, the inner diameter of the drive shaft 20 increases as a result of rotation. Meanwhile, since the second layer 24 holds the loosening first layer 23, the destruction of the drive shaft 20 that is attributable to an excessive loosening of the first layer 23 may be prevented. As a result, it is possible to prevent the phenomenon in which the drive shaft 20 grabs the protective tubular main body 71 (grabbing phenomenon) without destroying the drive shaft 20 in a state where torque acts on the drive shaft 20 as a two-layer structure. Accordingly, it is possible to prevent the rotation of the protective tubular main body 71 that follows the drive shaft 20. In accordance with an exemplary embodiment, the diameter of the wire rod of the first layer 23 may be equal to the diameter of the wire rod of the second layer 24. Alternatively, the diameter of the wire rod of the first layer 23 may be different from the diameter of the wire rod of the second layer 24. The cross-sectional shape of the wire rod of the first layer 23 and the cross-sectional shape of the wire rod of the second layer 24 are not limited to a perfect circle and may be, for example, an ellipse, a polygon, and so on.

Figure 9B:
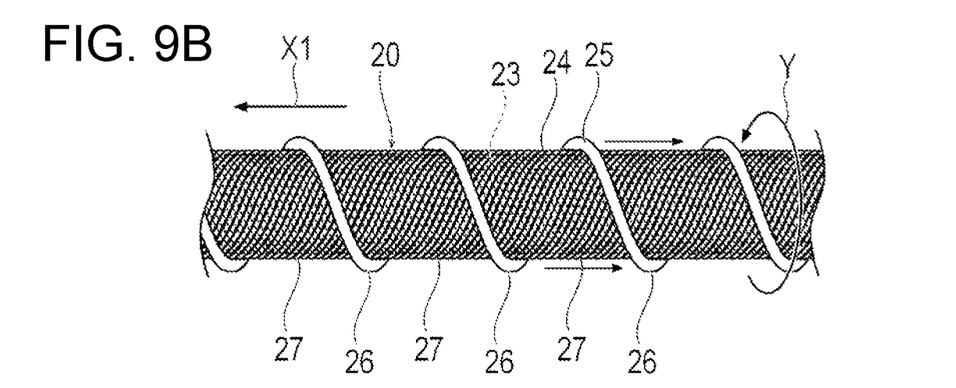

In addition, the drive shaft 20 may include a third layer 25 surrounding the outside of the second layer 24 as in a fifth modification example illustrated in FIG. 9B. The third layer 25 has one wire rod wound to the rotation direction Y side toward the distal direction X1. It should be noted that the third layer 25 may be formed by a plurality of wire rods. The cross-sectional shape of the wire rod of the third layer 25 is not limited to a perfect circle and may be, for example, an ellipse, a polygon, and so on. The wire rod of the third layer 25 is spirally wound so as to have a gap. Accordingly, the wire rod of the third layer 25 forms protruding portions 26 protruding radially outward on the outer surface of the second layer 24 and forms groove portions 27 between the adjacent protruding portions 26. When the drive shaft 20 rotates, the spiral third layer 25 is capable of transporting a fluid or the like to the proximal side in the tubular body (such as the outer tube 30) that accommodates the drive shaft 20. At this time, the wire rod of the third layer 25 is capable of effectively transporting the fluid or the like since it has a spiral shape having a gap. In addition, the third layer 25 may have one or more wire rods wound in the direction opposite to the rotation direction Y toward the distal direction X1. When the drive shaft 20 rotates in this case, the spiral third layer 25 is capable of transporting a fluid or the like to the distal side in the tubular body (such as the inner tube 50) that accommodates the drive shaft 20. The third layer 25 may have a wire rod wound in the forward direction of the rotation direction Y toward the distal direction X1 and a wire rod wound in the direction opposite to the rotation direction Y toward the distal direction X1 in ranges different in the axial direction X. It should be noted that the drive shaft 20 may have yet another layer.

In accordance with an exemplary embodiment, the drive shaft 20 may be a three-layer structure having the inner first layer 23, the outer third layer 25, and the second layer 24 between the first layer 23 and the third layer 25. The third layer 25 and the first layer 23 are wound to the rotation direction Y side toward the distal direction X1, and the second layer 24 is wound in the direction opposite to the rotation direction Y. The diameter of the wire rod of the third layer 25 may be larger than the diameter of the wire rod of the first layer 23 or the diameter of the wire rod of the second layer 24. The wire rod of the third layer 25 is spirally wound at a pitch larger than those of the first layer 23 and the second layer 24. As a result, when torque acts on the drive shaft 20, the inner diameter of the first layer 23 increases and the phenomenon in which the drive shaft 20 grabs the protective tubular main body 71 can be prevented. At the same time, the distance between the second layer 24 and the inner tube 50 or the outer tube 30 increases while the second layer 24 contracts in the radial direction to suppress an excessive loosening of the inner diameter of the first layer 23. A relatively wide space can be secured as a result. Accordingly, the fluid or the like between the second layer 24 and the inner tube 50 or the outer tube 30 can be smoothly transported to the proximal side by the spiral third layer 25 having a gap.

The detailed description above describes embodiments of a medical device for cutting an object in a body lumen. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object in a body lumen, the medical device comprising:
    a rotatable and tubular drive shaft;
    a cutting unit fixed to a distal portion of the drive shaft and having a through-hole communicating with a lumen of the drive shaft;
    a protective tubular main body accommodated in the drive shaft and the cutting unit, the protective tubular main body configured to be rotatable relative to the drive shaft;
    a handle configured to rotatably hold a proximal portion of the drive shaft, the handle including a casing and a handle-side stopper, the handle-side stopper being fixed to a proximal portion of the casing, and wherein a guidewire lumen of the protective tubular main body extends through the handle-side stopper;
    a protective-side stopper, the protective-side stopper being a projection on an outer peripheral surface of a distal portion of the protective tubular main body or a recess disposed in the outer peripheral surface of the distal portion of the protective tubular main body;
    the distal portion of the drive shaft or the cutting unit includes a drive-side stopper contactable with the protective-side stopper; and
    wherein the protective tubular main body is prevented from moving in an axial direction with respect to the drive shaft without being prevented from rotating relative to the drive shaft by the protective-side stopper coming into contact with the drive-side stopper.

2. The medical device according to claim 1, wherein
    the protective-side stopper includes a protective-side proximal surface facing a proximal direction;
    the drive-side stopper includes a drive-side proximal surface facing a distal direction, positioned on a proximal side of the protective-side proximal surface, and facing the protective-side proximal surface; and
    the protective tubular main body is prevented from moving in the proximal direction with respect to the drive shaft without being prevented from rotating relative to the drive shaft by the protective tubular main body moving in the proximal direction with respect to the drive shaft and the protective-side proximal surface coming into contact with the drive-side proximal surface.

3. The medical device according to claim 2, wherein a position of a most distal end of the protective tubular main body in the axial direction coincides with a position of a most distal end of the cutting unit or is closer to a distal side than the most distal end of the cutting unit in a state where the protective-side proximal surface is in contact with the drive-side proximal surface.

4. The medical device according to claim 1, wherein
    the protective-side stopper includes a protective-side distal surface facing the distal direction;
    the drive-side stopper includes a drive-side distal surface facing the proximal direction, positioned on a distal side of the protective-side distal surface, and facing the protective-side distal surface; and
    the protective tubular main body is prevented from moving in the distal direction with respect to the drive shaft without being prevented from rotating relative to the drive shaft by the protective tubular main body moving in the distal direction with respect to the drive shaft and the protective-side distal surface coming into contact with the drive-side distal surface.

5. The medical device according to claim 1, wherein the handle-side stopper is configured to prevent the protective tubular main body from rotating.

6. The medical device according to claim 5, wherein the handle-side stopper is configured to allow the protective tubular main body to move in an axial direction of the handle.

7. The medical device according to claim 6, further comprising:
    a protrusion disposed in a circumferential direction on an outer peripheral surface of the protective tubular main body;
    the handle-side stopper includes a holding portion sandwiching the protrusion in the circumferential direction; and
    the holding portion sandwiching the protrusion in the circumferential direction prevents the protective tubular main body and the handle-side stopper from rotating relative to each other and allows the protective tubular main body and the handle-side stopper to move relative to each other in the axial direction.

8. The medical device according to claim 6, wherein
the handle-side stopper includes a protrusion in a circumferential direction;
a holding portion sandwiching the protrusion in the circumferential direction and is disposed on an outer peripheral surface of the protective tubular main body; and
the holding portion sandwiching the protrusion in the circumferential direction and configured to prevent the protective tubular main body and the handle-side stopper from rotating relative to each other and configured to allow the protective tubular main body and the handle-side stopper to move relative to each other in the axial direction.

9. The medical device according to claim 1, wherein the handle includes a liquid delivering port configured to deliver a liquid from outside of the handle and the liquid delivering port communicates with a space between the protective tubular main body and the drive shaft and/or an inner side of the protective tubular main body.

10. The medical device according to claim 1, wherein
the drive shaft includes a first layer and a second layer surrounding an outer side of the first layer;
the first layer includes a wire rod wound in a forward direction of a rotation direction toward the distal direction; and
the second layer includes a wire rod wound in the direction opposite to the rotation direction toward the distal direction.

11. The medical device according to claim 10, wherein
the drive shaft includes a third layer surrounding an outer side of the second layer; and
the third layer includes a wire rod wound in a forward direction on the rotation direction side or the opposite direction toward the distal direction.

12. The medical device according to claim 11, wherein the wire rod of the first layer and the wire rod of the third layer are wound in the same direction toward the distal direction.

13. A method for cutting an object in a body lumen, the method comprising:
inserting a guide wire into the body lumen and reaching a vicinity of the object in the body lumen;
inserting a proximal end of the guide wire into a guide wire lumen of the medical device according to claim 1;
moving the cutting unit to the vicinity of the objection in the body lumen using the guide wire; and
rotating the drive shaft and cutting the object with the cutting unit.

14. The method according to claim 13, further comprising:
bending a distal portion of the medical device before inserting the medical device into the body lumen to change a position of the cutting unit in the body lumen, and wherein the protective tubular main body disposed in an outer tube of the medical device has a shape that matches a shape in which the outer tube is bent; and
causing the outer tube to reciprocate along a direction of elongation of the body lumen by moving an entirety of the handle or the outer tube exposed to an outside of the body lumen.

15. The method according to claim 13, further comprising:
flowing a saline solution to the vicinity of the object in the body lumen; and
aspirating the cut object and the saline solution via an aspiration lumen.

16. A medical device for cutting an object in a body lumen, the medical device comprising:
a rotatable and tubular drive shaft;
a cutting unit fixed to a distal portion of the drive shaft and having a through-hole communicating with a lumen of the drive shaft;
a protective tubular main body accommodated in the drive shaft and the cutting unit, the protective tubular main body configured to be rotatable relative to the drive shaft;
a protective-side stopper, the protective-side stopper being a projection on outer peripheral surface of a distal portion of the protective tubular main body;
the distal portion of the drive shaft or the cutting unit includes a drive-side stopper contactable with the protective-side stopper;
wherein the protective tubular main body is prevented from moving in an axial direction with respect to the drive shaft without being prevented from rotating relative to the drive shaft by the protective-side stopper coming into contact with the drive-side stopper; and
a handle configured to rotatably hold a proximal portion of the drive shaft, the handle including a casing and a handle-side stopper, the handle-side stopper being fixed to a proximal portion of the casing, and wherein a guidewire lumen of the protective tubular main body extends through the handle-side stopper.

17. The medical device according to claim 16, wherein
the handle-side stopper is configured to prevent the protective tubular main body from rotating, and the handle-side stopper is configured to allow the protective tubular main body to move in an axial direction of the handle;
a protrusion disposed in a circumferential direction on an outer peripheral surface of the protective tubular main body;
the handle-side stopper includes a holding portion sandwiching the protrusion in the circumferential direction; and
the holding portion sandwiching the protrusion in the circumferential direction prevents the protective tubular main body and the handle-side stopper from rotating relative to each other and allows the protective tubular main body and the handle-side stopper to move relative to each other in the axial direction.

18. The medical device according to claim 17, wherein the handle includes a liquid delivering port configured to deliver a liquid from outside of the handle and the liquid delivering port communicates with a space between the protective tubular main body and the drive shaft and/or an inner side of the protective tubular main body.

19. The medical device according to claim 16, wherein
the drive shaft includes a first layer and a second layer surrounding an outer side of the first layer;
the first layer includes a wire rod wound in a forward direction of a rotation direction toward the distal direction; and
the second layer includes a wire rod wound in the direction opposite to the rotation direction toward the distal direction.

20. A medical device for cutting an object in a body lumen, the medical device comprising:
a rotatable and tubular drive shaft;
a cutting unit fixed to a distal portion of the drive shaft and having a through-hole communicating with a lumen of the drive shaft;

a protective tubular main body accommodated in the drive shaft and the cutting unit, the protective tubular main body configured to be rotatable relative to the drive shaft;

a protective-side stopper, the protective-side stopper being a recess in outer peripheral surface of a distal portion of the protective tubular main body;

the distal portion of the drive shaft or the cutting unit includes a drive-side stopper contactable with the protective-side stopper;

wherein the protective tubular main body is prevented from moving in an axial direction with respect to the drive shaft without being prevented from rotating relative to the drive shaft by the protective-side stopper coming into contact with the drive-side stopper; and a handle configured to rotatably hold a proximal portion of the drive shaft, the handle including a casing and a handle-side stopper, the handle-side stopper being fixed to a proximal portion of the casing, and wherein a guidewire lumen of the protective tubular main body extends through the handle-side stopper.

* * * * *